US00PP32632P3

(12) United States Plant Patent
Post

(10) Patent No.: US PP32,632 P3
(45) Date of Patent: Dec. 15, 2020

(54) ***CHRYSANTHEMUM* PLANT NAMED 'DLFCHIA4'**

(50) Latin Name: ***Chrysanthemum* X *morifolium***
Varietal Denomination: DLFCHIA4

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 16/873,327

(22) Filed: Mar. 19, 2020

(65) Prior Publication Data

US 2020/0305330 P1 Sep. 24, 2020

Related U.S. Application Data

(60) Provisional application No. 62/919,611, filed on Mar. 20, 2019.

(51) Int. Cl.
*A01H 5/02* (2018.01)
*A01H 6/14* (2018.01)

(52) U.S. Cl.
USPC ..... Plt./293
CPC ..... *A01H 6/1424* (2018.05)

(58) Field of Classification Search
USPC ..... Plt./293
CPC ... A01H 5/02; A01H 5/00; A01H 6/14; A01H 6/1424
See application file for complete search history.

*Primary Examiner* — June Hwu
(74) *Attorney, Agent, or Firm* — C. A. Whealy

(57) ABSTRACT

A new and distinct cultivar of *Chrysanthemum* plant named 'DLFCHIA4', characterized by its upright plant habit; vigorous growth habit; freely branching habit; dark green-colored leaves; uniform and freely flowering habit; strong upright flowering stems with numerous inflorescences; decorative-type inflorescences with dark red-colored ray florets; and relative resistance to *Fusarium oxysporum* f. sp. *chrysanthemi*.

2 Drawing Sheets

Figure 1:
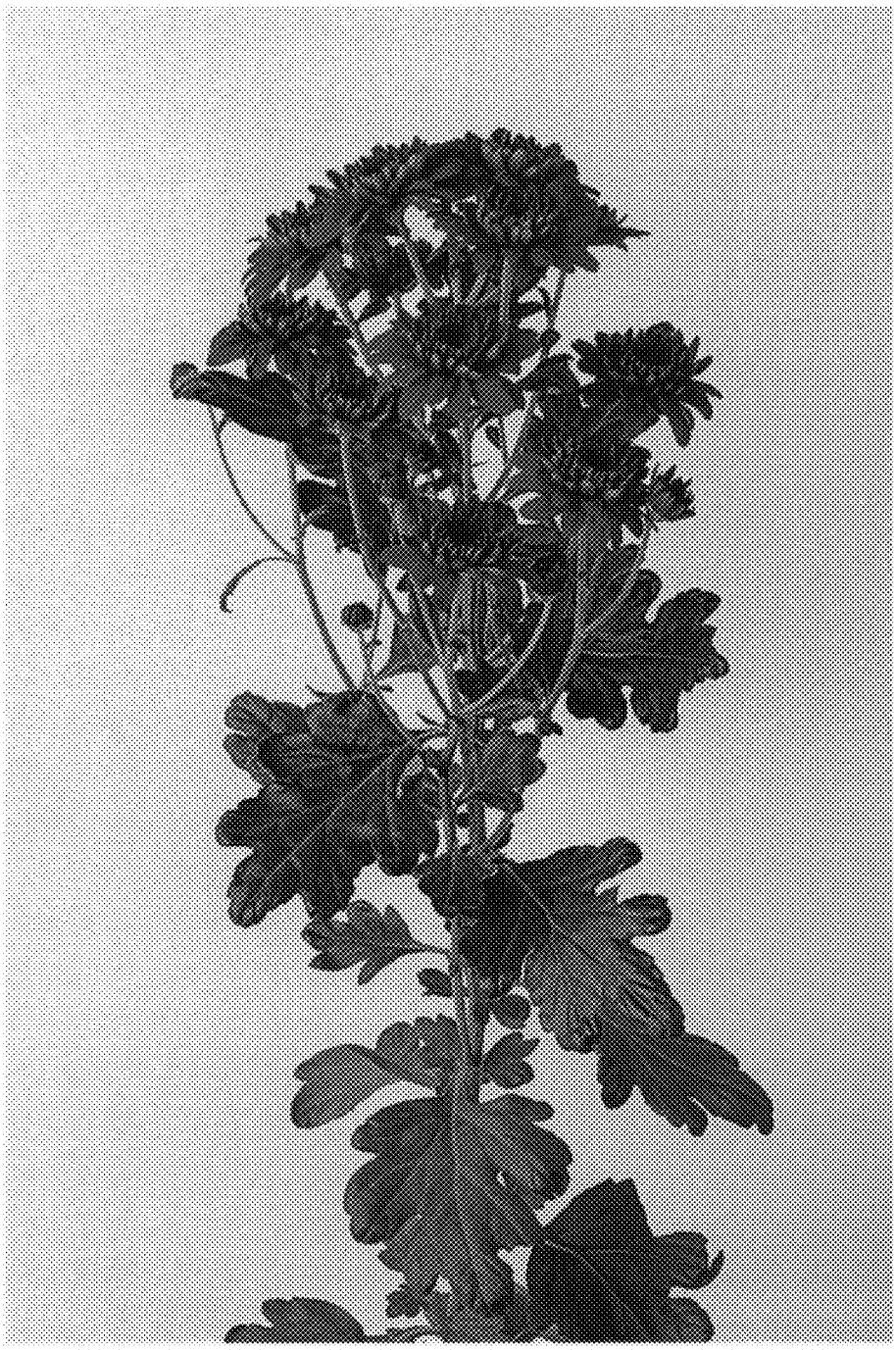

Botanical designation: *Chrysanthemum* X *morifolium*.
Cultivar denomination: 'DLFCHIA4'.

CROSS-REFERENCED TO CLOSELY-RELATED APPLICATIONS

Title: Varieties of *Chrysanthemum* Plants
Inventor/Applicant: Arie Gerard Post
Filed: Mar. 20, 2019
Ser. No. 62/919,611

Inventor/Applicant hereby claim the benefit of this provisional U.S. Patent Application. &cl STATEMENT REGARDING PRIOR DISCLOSURES BY INVENTOR/APPLICANT & ASSIGNEE An European Community Plant Breeder's Rights application for the instant plant was filed by the Assignee, Delitlor Royalties B. V. of Maasdijk, The Netherlands on Nov. 19, 2018, application number 2018/3025. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFCHIA4'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant originated from a cross-pollination in February, 2015 'Delibarca', not patented as the female, or seed, parent with a proprietary selection of *Chrysanthemum* x *morifolium* identified as code number DB 42809 as the male; or pollen, parent. The new *Chrysanthemum* plant was discovered and selected as a single flowering plant from within the progeny of the stated cross-pollination in a controlled greenhouse environment in Maasdijk, The Netherlands in April, 2016.

Asexual reproduction of the new *Chrysanthemum* plant by vegetative terminal cuttings since April, 2016 in Maasdijk, The Netherlands has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFCHIA4'. These characteristics in combination distinguish 'DLFCHIA4' as a new and distinct *Chrysanthemum* plant:

1. Upright plant habit; vigorous growth habit.
2. Freely branching habit.
3. Dark green-colored leaves.
4. Uniform and freely flowering habit.
5. Strong upright flowering stems with numerous inflorescences.
6. Decorative-type inflorescences with dark red-colored ray florets.
7. Relatively resistant to *Fusarium oxysporum* f. sp. *chrysanthemi*.

Plants of the new *Chrysanthemum* differ from plants of the female parent, 'Delibarca', in inflorescence size as plants of the new *Chrysanthemum* have larger inflorescences than plants of the female parent, 'Delibarca'. In addition, plants of the new *Chrysanthemum* have dark red-colored ray florets whereas plants of the female parent, 'Delibarca' have dark purplish red-colored ray florets.

Plants of the new *Chrysanthemum* differ from plants of the male parent selection in ray floret color as plants of the new *Chrysanthemum* have lighter red-colored ray florets than plants of the male parent selection. In addition, ray florets of plants of the new *Chrysanthemum* have retuse to emarginate-shaped apices whereas ray florets of plants of the male parent selection have obtuse-shaped apices.

Plants of the new *Chrysanthemum* can be compared to plants of *Chrysanthemum* X *morifolium* 'Delibarca Red', not patented. In side-by-side comparisons plants of the new *Chrysanthemum* differ primarily from plants of 'Delibarca Red' in ray floret color as ray florets of plants of the new *Chrysanthemum* are lighter red in color than ray florets of plants of 'Delibarca Red'. In addition, ray florets of plants of the new *Chrysanthemum* are slightly convex in cross-section whereas ray florets of plants of 'Delibarca Red' are slightly concave in cross-section.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1 of 2) comprises a side perspective view of a typical flowering stem of 'DLFCHIA4' grown as a spray-type cut flower.

Figure 2:
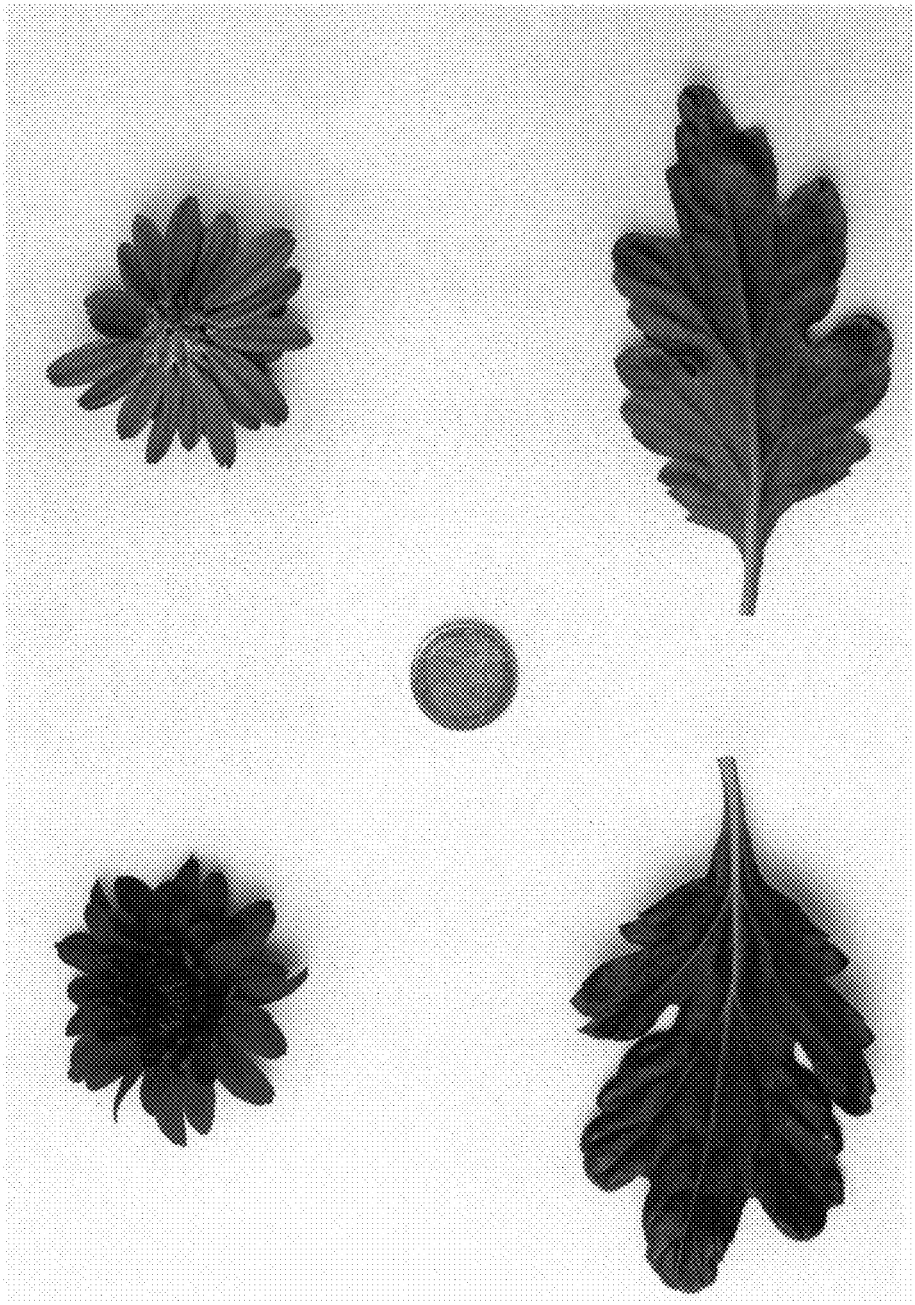

The photograph on the second sheen (FIG. 2 of 2) is a close-up view of lower (top of the photographic sheet) and upper (bottom of the photographic sheet) surfaces of typical inflorescences (left) and leaves (right).

DETAILED BOTANICAL DESCRIPTION

The aforementioned photographs and following observations and measurements describe plants grown during the winter in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 2° C. to 20° C. and light levels averaged 8 klux. Plants were grown as single-stem spray-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFCHIA4'.

Parentage:

*Female, or seed, parent*.—'Delibarca', not patented.

*Male, or pollen, parent*.—Proprietary selection of *Chrysanthemum* x *morifolium* identified as code number DB 42809, not patented.

Propagation:

*Type*.—Terminal vegetative cuttings.

*Time to initiate roots, summer*.—About six days at temperatures about 24° C.

*Time to initiate roots, winter*.—About eight days at temperatures about 22° C.

*Time to produce a rooted young plant, summer*.—About twelve days at temperatures about 24° C.

*Time to produce a rooted young plant, winter*.—About two weeks at temperatures about 22° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem spray-type; upright plant habit; vigorous growth habit and rapid growth rate.

*Plant height, soil level to top of foliar plane*.—About 80.3 cm.

*Plant height, soil level to top of inflorescence plane*.—About 83.4 cm.

*Plant (spray) diameter*.—About 18.8 cm.

*Flowering stem length*.—About 76.2 cm.

*Flowering stem diameter*.—About 7 mm.

*Flowering stem internode length*.—About 3.2 cm.

*Flowering stem strength*.—Strong.

*Flowering stem aspect*.—Erect.

*Flowering stem texture and luster*.—Moderately pubescent; slightly glossy.

*Flowering stem color, developing*.—Close to 143B.

*Flowering stem color, developed*.—Close to between 143A and 146B; ridges, tinged with close to 183B.

*Leaf description*.—Arrangement: Alternate; simple. Length: About 12.2 cm. Width: About 8.5 cm. Shape: Ovate to broadly ovate. Apex: Short apiculate. Base: Attenuate. Margin: Palmately lobed, coarsely crenate; sinuses convergent and medium in depth. Texture and luster, upper surface: Moderately pubescent, not rugose; moderately velvety; very slightly glossy. Texture and luster, lower surface: Moderately pubescent, prominent venation; slightly velvety; matte. Venation pattern: Pinnate, reticulate. Color: Developing leaves, upper surface: Close to between 137B and 143A, closest to 137B. Developing leaves, lower surface: Close to 138B. Fully developed leaves, upper surface: Close to NN137A; venation, close to 147C. Fully developed leaves, lower surface: Close to 147B; venation, close to 146C. Petioles: Length: About 1.7 cm. Diameter: About 2.5 mm by 3 mm.

Strength: Moderately strong. Texture and luster, upper and lower surfaces: Densely pubescent; slightly glossy. Color, upper surface: Close to 147C; edges, close to NN137B. Color, lower surface: Close to 146C; edges, close to 137A. Stipules: Quantity and appearance: Two leafy stipules, opposite, at the petiole attachment to the stem. Length: About 1.5 cm. Width: About 1.9 cm. Shape: Flabellate. Texture and luster, upper surface: Moderately pubescent, not rugose; moderately velvety; very slightly glossy. Texture and luster, lower surface: Moderately pubescent, prominent venation; slightly velvety; matte. Color, upper surface: Close to NN137A. Color, lower surface: Close to 147B.

Inflorescence description:

*Appearance*.—Decorative inflorescence form with oblanceolate-shaped ray florets and tubular disc florets (disc florets are inconspicuous); inflorescences borne perpendicular to peduncles and face mostly upright to slightly outwardly; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 52 days later when grown as a spray-type.

*Postproduction longevity*.—Good postproduction longevity; in an interior environment, inflorescences and foliage will maintain good color and substance for about two weeks; inflorescences persistent.

*Quantity of inflorescences*.—Freely flowering habit; when grown as a spray-type, about 17 inflorescences develop per flowering stem.

*Inflorescence size*.—Diameter: About 7.5 cm. Depth (height): About 2.5 cm. Disc diameter: About 3 mm.

*Receptacles*.—Height: About 4 mm. Diameter: About 5 mm. Shape: Flattened globular. Color: Close to 144C.

*Inflorescence buds*.—Height: About 9 mm. Diameter: About 1 cm. Shape: Roughly globular. Texture and luster: Distally, smooth and glabrous; proximally, moderately pubescent; slightly glossy. Color: Close to 138C and 143A; immature ray florets, close to 183B.

*Ray florets*.—Quantity and arrangement: About 280 arranged in about eight whorls. Length: About 2.4 cm; varying between 0.8 cm and 3.4 cm. Width: About 6 mm; varying between 1 mm and 9 mm. Shape: Oblanceolate; slightly concave and carinate. Apex: Retuse to emarginate. Base: Attenuate. Margin: Entire; not undulate. Aspect: Initially upright to about 90° from vertical. Texture and luster, upper surface: Smooth, glabrous; velvety; matte. Texture and luster, lower surface: Smooth, glabrous; moderately velvety; slightly glossy. Color: When opening, upper surface: Close to 53A. When opening, lower surface: Close to 178B. Fully opened, upper surface: Close to 53A; venation, close to 53A; color does not change with development. Fully opened, lower surface: Close to 181B; venation, close to 184A; color does not change with development.

*Disc florets*.—Quantity and arrangement: About twelve spirally arranged in about two whorls at the center of the receptacle; disc florets inconspicuous. Length: About 3 mm. Diameter: About 1 mm. Shape: Lower 75% fused into a tube; upper 25% free. Apex: Narrowly acute. Margin, distally: Entire. Texture and luster, inner and outer surfaces: Smooth, glabrous; glossy. Color, when opening, inner and outer surfaces: Apex: Close to 144B. Mid-section: Close to 145D. Base: Close to 145C. Color, fully opened, inner and outer surfaces: Apex: Close to 144B. Mid-section: Close to 145D. Base: Close to 145C.

*Involucral bracts*.—Quantity and arrangement: About 24 arranged in two whorls. Length: About 7 mm. Width: About 3 mm. Shape: Ovate. Apex: Obtuse. Base: Cuneate. Margin: Entire. Texture and luster, upper surface: Smooth, glabrous; glossy. Texture and luster, lower surface: Densely pubescent; matte. Color, upper surface: Close to 143A; margins, translucent and close to 145C. Color, lower surface: Close to 137C; margins, translucent and close to 145C.

*Peduncles*.—Length, terminal peduncle: About 5.4 cm. Diameter, terminal peduncle: About 2 mm. Length, third peduncle: About 6.8 cm. Diameter, third peduncle: About 2 mm. Strength: Strong. Aspect, terminal peduncle: Mostly upright. Aspect, third peduncle: About 25° from the flowering stem axis. Texture and luster: Densely pubescent; matte. Color: Close to 137C.

*Reproductive organs*.—Androecium: Present on disc florets only. Quantity: About five per floret. Filament length: About 1.5 mm. Filament color: Close to 145D. Anther size: About 0.5 mm by 0.75 mm. Anther shape: Narrowly oblong. Anther color: Close to 13A. Pollen amount: Scarce. Pollen color: Close to 14B. Gynoecium: Present on both ray and disc florets. Quantity: One per floret. Pistil length: About 4 mm. Style length: About 3.5 mm. Style color: Close to 144C. Stigma diameter: About 1 mm. Stigma shape: Cleft, decurrent. Stigma color: Close to 151D. Ovary color: Close to 145C.

*Seeds and fruits*.—To date, seed and fruit production have not been observed on plants of the new *Chrysanthemum*.

Pathogen & pest resistance: Plants of the new *Chrysanthemum* have been observed to be relatively resistant to *Fusarium oxysporum* f. sp. *chrysanthemi*. To date, plants of the new *Chrysanthemum* have not been observed to be resistant to pests and other pathogens common to plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFCHIA4' as illustrated and described.

* * * * *